United States Patent [19]
Lee

[11] Patent Number: 5,312,355
[45] Date of Patent: * May 17, 1994

[54] SPLITTABLE HEMOSTATIC VALVE AND SHEATH AND THE METHOD FOR USING THE SAME

[75] Inventor: Hongpyo Lee, Rancho Palos Verdes, Calif.

[73] Assignee: H L Medical Inventions, Inc., Rancho Palos Verdes, Calif.

[*] Notice: The portion of the term of this patent subsequent to Jun. 30, 2009 has been disclaimed.

[21] Appl. No.: 905,045

[22] Filed: Jun. 26, 1992

Related U.S. Application Data

[63] Continuation-in-part of Ser. No. 727,191, Jul. 9, 1991, Pat. No. 5,125,904.

[51] Int. Cl.⁵ .............................. A61M 5/178
[52] U.S. Cl. .................... 604/160; 604/164; 604/161
[58] Field of Search ............... 604/167, 169, 160, 161, 604/256, 164, 200, 201, 202, 205, 236, 905, 166, 165, 264; 251/149.1; 137/843, 844, 845, 849

[56] References Cited

U.S. PATENT DOCUMENTS

| | | | |
|---|---|---|---|
| 3,653,388 | 4/1972 | Tenckhoff | 604/161 |
| 3,677,244 | 7/1972 | Hassinger | 604/161 |
| 4,345,596 | 8/1982 | Young | 604/161 |
| 4,596,559 | 6/1986 | Fleischhacker | 604/161 |
| 4,747,833 | 5/1988 | Kousai et al. | 604/161 |
| 4,772,266 | 9/1988 | Groshong | 604/164 |
| 4,921,479 | 5/1990 | Grayzel | 604/164 |
| 4,960,412 | 10/1990 | Fink | 604/167 |

Primary Examiner—John G. Weiss
Assistant Examiner—Nicholas D. Lucchesi
Attorney, Agent, or Firm—Daniel L. Dawes

[57] ABSTRACT

A splittable hemostatic valve and introducer sheath is provided for introductions of leads or catheters through the valve and sheath combination into a vein or artery. Because of the hemostatic valve, this sheath can remain in the vein throughout the operation with the advantage of free lead exchange possibility and easier lead manipulation, especially in dual lead insertions, without bleeding, risk of air embolism or repeated sheath insertion related trauma for lead exchange. A side arm to the hemostatic valve cage provides continuous fluid drip in order to prevent clot formation in the lumen of the sheath. At the point in the operation where the introducer sheath and hemostatic valve must be removed from the lead or catheter, which must remain implanted, a device is employed to split or separate the introducer sheath and valve apart so that the sheath and valve are removed from the implanted lead or catheter without the necessity of sliding either the sheath or valve over the free end of the lead or catheter. The hemostatic valve is made in two separate parts which include a fluid-tight seal to facilitate splitting of the valve. In this manner, any termination which may be provided on the free end of the lead or catheter, such as a terminal for connection to a pacemaker, will not interfere with the optimal use of the introducer sheath and hemostatic valve.

33 Claims, 3 Drawing Sheets

SPLITTABLE HEMOSTATIC VALVE AND SHEATH AND THE METHOD FOR USING THE SAME

RELATED APPLICATIONS

The present application is a continuation-in-part application of copending application Ser. No. 07/727,191 filed Jul. 9, 1991, and and issued Jun. 30, 1992 U.S. Pat. No. 5,125,904.

BACKGROUND OF THE INVENTION

1. Field of the Invention

The invention relates to the field of pacemaker leads and catheters and methods for insertion of the same, and in particular to leads used in veins such as in connection with pacemaker procedures such as pacemaker lead insertion.

2. Description of the Prior Art

There are many medical procedures which require a puncture and catherterization of an artery or vein for various purposes.

In the prior art process of percutaneous puncture, a guidewire is introduced into the vessel through a hollow needle. The needle is withdrawn leaving the guidewire in the vessel. A TEFLON dilator and venous sheath assembly are then advanced in a rotary motion over the guidewire into the vessel. The TEFLON dilator and the guidewire are then removed leaving the flexible sheath in the vessel. At this point, various types of catheters or leads are inserted using the sheath as a conduit to avoid tearing or further trauma to the vessel wall.

In the case where a pacemaker lead must be permanently inserted into the patient, the pacemaker is subcutaneously implanted in the patient and the lead, which extends from the pacemaker into the heart chamber, remains permanently disposed through the vessel wall and in the vessel lumen. A sheath is nevertheless used in order to guide insertion of the lead into vein lumen, but must be removed leaving the lead in place. However, the sheath cannot simply, in all cases, be slipped over the exterior end of the pacemaker lead which may be provided with a special termination for connection to the pacemaker.

In this case, the prior art has devised a number of splittable or peel away sheaths. The sheath is scored so that it is withdrawn by splitting or peeling it off from the pacemaker catheter. See Philip 0. Littleford, et al, "The American Journal of Cardiology," Vol. 43, pp. 980–982 (May 1979); Littleford, "Apparatus and Method for Inserting an Electrode," U.S. Pat. No. 4,166,469 (1979); Littleford, "Method for Inserting Pacemaker Electrodes and the Like," U.S. Pat. No. 4,243,050 (1981) and Littleford," "Split Sleeve Introducers for Pacemaker Electrodes and the Like," U.S. Pat. No. Re. 31,855 (1985), a reissue of U.S. Pat. No. 4,306,562 (1981); Boarini et al., "Peelable Catheter with Securing Ring and Suture Sleeve," U.S. Pat. No. 4,411,654 (1983); Moorehead, "Medical Layered Peel Away Sheath and Methods," U.S. Pat. No. 4,983,168 (1991). A splittable cannula is also taught by Kousai et al., "Medical Tool Introduction Cannula and Method of Manufacturing the Same," U.S. Pat. No. 4,883,468 (1989).

However, in each of these prior art sheath assemblies, once the sheath has been inserted the sheath provides a passage for the free flow of blood. In practice a significant amount of bleeding may occur at the operation site, which requires constant mopping and cleaning. The amount of loss of blood during an operation may begin to have a negative impact upon the patient.

Secondly, in addition to the sheath assembly providing an open passage for the loss of blood, the sheath assembly also provides an open passage for the introduction of air into the vein. The inadvertent introduction of air into the blood system causes air embolism in the patient and its consequent negative effects.

Thirdly, clotting may be formed in the lumen of the sheath if the sheath remains in for a prolonged time, and this may cause embolism to the lung and its consequent negative effects.

Because of the three problems above, the prior art splittable sheath has to be removed as soon as the lead is introduced into the vessel lumen, although it is very desirable to retain the sheath in place throughout operation because the lead can be manipulated much easier without interference from other existing lead or tissue friction and can be exchanged freely without repeated sheath insertion trauma.

When the catheter or lead is introduced in the sheath, a certain amount of blood leakage will occur between the catheter and the sheath walls. The prior art has also devised hemostatic valves which provide a seal around the catheter introduced through the sheath. One such sheath and hemostatic valve is manufactured and marketed by Cordis Corp. of Miami, Fla. as the UNISTA-SIS valve in the Cordis catheter sheath introducer. Another example is manufactured by Bard of Billerica, Mass. as the 5F HEMAQUET introducer. A hemostatic valve combined with a splittable sheath is also illustrated in Schiff, "Introducer Assembly for Intra-Aortic Balloons and the Like Incorporating a Sliding, Blood-Tight Seal," U.S. Pat. No. 4,473,067 (1984).

However, all the prior art hemostatic valve structures, even when combined with a splittable sheath, such as shown by Schiff, are integral or rigid units, which do not split and must be removed by sliding along the end of the catheter. In the case of Schiff, the sheath is split in order to appropriately position the balloon catheter. However, after the balloon angioplasty procedure is completed, the entire catheter is removed so that at no point is the hemostatic valve entirely removed from the catheter nor need it be.

What is needed then is some type of sheath and valve system which can be used in connection with our vessel introducers, which introducers can then remain in place without risking undue bleeding, air embolism, or clotting while retaining the advantages of an introducer sheath for free lead exchange and easier lead manipulation.

BRIEF SUMMARY OF THE INVENTION

The invention is a sheath assembly for use with a lead or catheter comprising an introducer sheath, and a hemostatic valve coupled to the introducer sheath. The hemostatic valve and introducer sheath are arranged and configured to permit introduction of at least one lead or catheter therethrough. An element is provided to permit removal of the hemostatic valve and introducer sheath from the catheter disposed therethrough without requiring the introducer sheath and hemostatic valve to be removed from an end of the catheter. A side arm is connected to the hemostatic valve cage and provides continuous fluid drip in order to prevent clot formation in the sheath lumen.

As a result, the assembly may safely remain in the vessel lumen throughout the operation without substantial bleeding, risk of air embolism, clotting, or need of repeated sheath insertion for lead exchange.

The element for permitting removal of the hemostatic valve and introducer sheath is a element for splitting the introducer sheath and hemostatic valve away from the lead or catheter which is disposed therethrough.

Alternatively, the element for permitting removal of the introducer sheath and the hemostatic valve is a element for peeling away the introducer sheath and hemostatic valve from the lead or catheter disposable therethrough.

In the illustrated embodiment the element for permitting removal of the hemostatic valve and introducer sheath is a score line defined in the hemostatic valve and introducer sheath along which the hemostatic valve and introducer sheath may be separated. The score line comprises a pair of lines defined in the hemostatic valve and introducer sheath. The pair of score lines are diametrically opposed from each other on the hemostatic valve and introducer sheath. The score line is disposed along the longitudinal length of the hemostatic valve and introducer sheath. The score line defined into the introducer sheath is aligned with the score line defined into the hemostatic valve.

The introducer sheath and hemostatic valve are integrally formed and the element for permitting removal of the valve and sheath permits removal of the valve and sheath as an integral body from the catheter disposed therethrough.

In another embodiment the introducer sheath and hemostatic valve are separate body portions coupled to each other and the element for permitting removal of the valve and sheath from the lead or catheter allow separate removal of the hemostatic valve and sheath from the lead or catheter.

The hemostatic valve is self sealing. The hemostatic valve and sheath are arranged and configured to allow the insertion therethrough of multiple leads or catheters. The hemostatic valve further comprises an intravenous sidearm assembly. The element for permitting removal of the hemostatic valve and sheath leaves the sidearm assembly intact.

The invention is also characterized as a method of percutaneous sheath lead or catherterization comprising the steps of disposing an introducer sheath and hemostatic valve coupled to the introducer sheath into a body lumen. At least one lead or catheter is disposed through the valve and introducer sheath into the body lumen. The lead or catheter is sealed within the hemostatic valve to prevent bleeding and introduction of air into the body lumen with disposition of the lead or catheter therein. The hemostatic valve and introducer sheath is removed while leaving the lead or catheter in place within the body lumen without sliding either the introducer sheath or hemostatic valve over an end of the lead or catheter. As a result, implanted leads or catheters may be disposed into the body lumen without bleeding, risk of air embolism, clotting or requiring the end of the lead or catheter to have a structure to permit removal of the sheath and valve thereover.

The step of removing the sheath and lead or catheter comprises the step of splitting the sheath and valve along a longitudinal length of the sheath and valve and disposing the lead or catheter radially through the longitudinal split.

More particularly, the step of splitting the sheath and valve comprises a step of splitting the sheath and valve along a score line by manually tearing the sheath and valve apart along the score line.

The step of tearing the sheath and valve along a score line further comprises tearing the sheath and valve along a pair of longitudinally defined score lines in the sheath and valve. The step of tearing the valve and sheath along a pair of score lines comprises in turn the step of tearing the valve and sheath along diametrically opposing longitudinally defined score lines in the valve and sheath respectively.

The invention is still further characterized as an improvement in an introducer sheath and valve assembly for implantation of pacemaker leads comprising an element for splitting the introducer sheath. The sheath has a longitudinal axis. The element for splitting allows manual separation of the sheath along the longitudinal axis. An other element for separating the hemostatic valve permits removal of the valve from the lead without necessitating removal of the valve over an end of the lead. As a result, the sheath can remain in place throughout the operation with the advantage of free lead exchange and easier lead manipulation without bleeding, air embolism, clotting and repeated sheath related trauma for possible lead exchange.

The invention is also a sheath assembly in which the element for permitting removal of the hemostatic valve and introducer sheath is a two-part body comprising the hemostatic valve. The two-part body is made in two separate body portions. The body portions define an element for sealing the body portions together when the two body parts are joined with each other to form the hemostatic valve.

The hemostatic valve comprises a resealable membrane. The element for permitting the removal of the hemostatic valve and introducer sheath comprises a cut in the in resealable membrane to facilitate parting of the membrane wherein the body portions are pulled apart.

The cut is a Y-shaped cut extending partially through the membrane. The intersection of the Y-shaped cut is positioned approximately near the center of the membrane with one leg of the Y extending toward the periphery of the membrane in a direction along which the membrane will be separated when the portions are pulled apart.

The element for sealing the body portions together comprises a circumferential sealing lip on each of the body portions. The sealing lip on one body portion conforming with the sealing lip on the other body portion to make the hemostatic valve fluid-tight when the body portions are temporarily joined together.

The sealing lip on one body portion is an inner circumferential sealing lip, and the sealing lip on the other body portion is an outer circumferential sealing lip. The inner and outer circumferential sealing lips conform with each other to seal the hemostatic valve.

The body portions further comprise at least one band of circumferential tape wound around the two-body portions to temporarily maintain the body portions together and to maintain the inner and outer circumferential sealing lips in a sealed configuration.

The inner and outer sealing lips tightly slip-fit together to maintain the two body portions temporarily joined to comprise the hemostatic valve until pried apart.

The body portion having one of the circumferential sealing lips forms a lid and the body portion having the other one of the circumferential sealing lips forms an enclosure having one open side. The body portion forming the lid joins the body portion forming the enclosure to provide a temporarily fluid-tight hemostatic valve body.

In one embodiment the inner circumferential sealing lip forms a tongue and wherein the outer circumferential sealing lip forms a groove. The tongue is tightly slip-fit into the groove to form a sealed relationship between two the body portions.

The sheath assembly further comprises a recess defined in one of the body portions to allow insertion of a flat blade therein to pry apart the two body portions.

In another embodiment the inner and outer circumferential sealing lips lock together by engagement with each other to seal the hemostatic valve.

In another embodiment the inner circumferential sealing lip has a knife edge and the outer circumferential sealing lip has a cavity defined therein conforming to the knife edge of the other sealing lip. The knife edge and cavity mate to form the seal of the hemostatic valve. The knife edge has an enlarged head. The enlarged head is snap-fit into a conforming enlargement defined in the cavity to lock the knife edge in the cavity.

The invention is also a method for percutaneous catherterization in which during the step of removing the hemostatic valve, the hemostatic valve is comprised of two body portions. The body portions are separately provided to form the hemostatic valve and are temporarily joined together to form a complete body of the hemostatic valve. The body portions are pulled apart to split the hemostatic valve.

The invention is better visualized by now turning to the following drawings wherein like elements are referenced by like numerals.

BRIEF DESCRIPTON OF THE DRAWINGS

FIG. 6 is a perspective view of the diaphragm of the hemostatic valve of FIG. 5 shown in isolation of all remaining elements.

FIG. 7a and b is a perpendicular cross-sectional view of the valve of FIGS. 4 and 5 as seen through sectional line 7—7 of FIG. 5. FIG. 7a shows the valve body assembled and closed with tape as shown in FIG. 4, while FIG. 7b shows the tape removed and valve body halves separated.

The invention and its various embodiments may now be understood by turning to the following detailed description.

DETAILED DESCRIPTION OF THE PREFERRED EMBODIMENTS

An improved hemostatic valve and introducer sheath is provided for introductions of leads or catheters through the valve and sheath combination into a vessel or artery. At the point in the operation where the introducer sheath and hemostatic valve must be removed from the lead or catheter, which must remain implanted, means are employed to split or separate the introducer sheath and valve apart so that the sheath and valve are removed from the implanted lead or catheter without the necessity of sliding either the sheath or valve over the free end of the lead or catheter. The hemostatic valve is made in two separate parts which include a fluid-tight seal to facilitate splitting of the valve. In this manner, any termination which may be provided on the free end of the lead or catheter, such as a terminal for connection to a pacemaker, will not interfere with tho optimal use of the introducer sheath and hemostatic valve.

Figure 1:
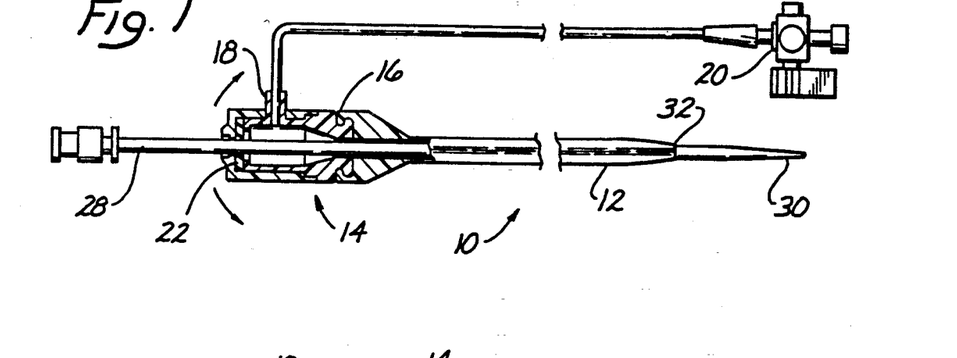
FIG. 1 is a partially cutaway side view of a splittable introducer sheath devised according to the invention.
Figure 2:
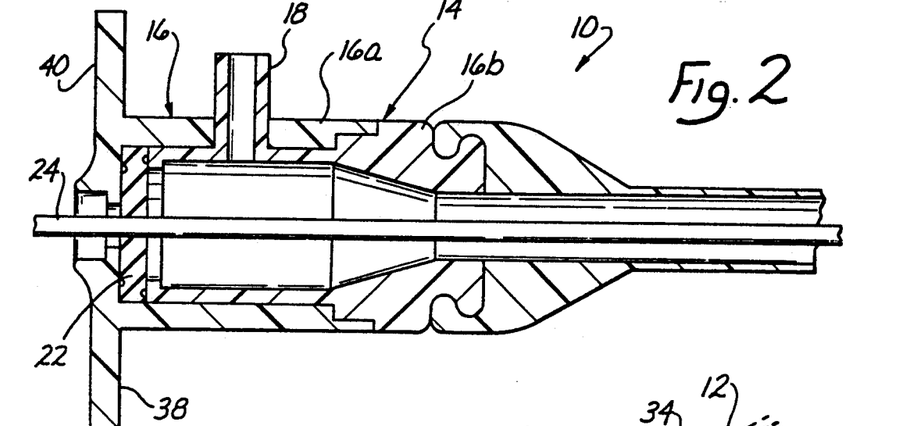
FIG. 2 is an enlargement of the splittable valve portion shown in FIG. 1 wherein a lead or catheter has been disposed through the valve.

A splittable introducer sheath and valve assembly, generally noted by reference numeral 10 in FIG. 1, is depicted in partially cutaway side view. Valve and sheath assembly 10 comprise a splittable sheath 12 connected, coupled or extending from a splittable hemostatic valve assembly 14. Valve assembly 14 in turn is comprised of a valve body 16, an intravenous sidearm 18 with a sidearm of valve 20. The details of the design of sidearm valve 20 and to a certain extent sidearm 18 are largely inconsequential to the present invention and therefore will not be further described except insofar as necessary to illustrate the invention. Hemostatic valve assembly 14 is shown in FIG. 1 in cutaway view exposing the interior of valve 16 which includes a valve membrane 22. The details of valve assembly 14 again are not critical to an understanding of the invention, but in the preferred embodiment, valve membrane 22 is a self-healing membrane through which a lead or catheter may be introduced without leakage between membrane 22 and leads or lead 24 such as shown in the partially cutaway view of FIG. 2 depicted in expanded scale. Valve body 16 in the illustrated embodiment is comprised of two sections 16a and b which are bonded together after assembly.

In the depiction of FIG. 1, a conventional dilator 28 is shown as disposed through valve assembly 14 and sheath 12 having a tapered tip 30 extending from the distal end 32 of sheath 12. As in the conventional methodology described above in connection with percutaneous sheath lead or catherterization, the artery or vessel is punctured with a needle into which a guidewire is placed. The needle removed and then dilator and sheath assembly 12 advanced on the guidewire into the vessel. The guidewire will extend through valve assembly 14 and be sealed by means of membrane 22. The guidewires and TEFLON dilator are then removed leaving the flexible sheath assembly 10 in place. However virtually no bleeding occurs since the entire assembly is sealed by self-healing membrane 22. At this point one or more leads or catheters as suggested in FIG. 2 can be introduced, removed and reintroduced and manipulated without any significant possibility of bleeding, clotting, risk of air embolism or repeated sheath insertion related trauma since once inserted sheath assembly 10 is in place regardless of the number of leads or catheters inserted and removed throughout the operation.

In addition, since sealing of leads or catheters 24 and 26 is effectuated by membrane 22 of valve assembly 14, valve body 16 and at least a portion of sheath 12 may be made larger than normal to allow a more loose fit between the interior surfaces of introducer sheath assembly 10 and leads or catheters 24 and 26, since blood sealing between the lead or catheter and sheath 12 is not required. This allows leads or catheters 24 and 26 to be introduced and removed from introducer sheath assembly 10 with less friction or interference with assembly 10 and with each other. Therefore the lead can be manipulated much easier.

The detailed construction of sheath 12 and valve assembly 14 as previously implied is not critical to the invention, at least to the extent of whether sheath 12 and valve assembly 10 must be separate or integral parts or how they may be connected with each other. Therefore, it must be expressly understood that valve assembly 14 and sheath 12 may be fabricated according to any structure or out of any material now known to the art or later devised without departing from the spirit and scope of the invention. For example, sheath 12 may be integrally molded or cast with valve assembly, may be adhesively affixed thereto, may be compression fitted, slip fit, threaded, or connected in any manner desired to valve assembly 14 consistent with the teachings of the present invention.

Figure 3:
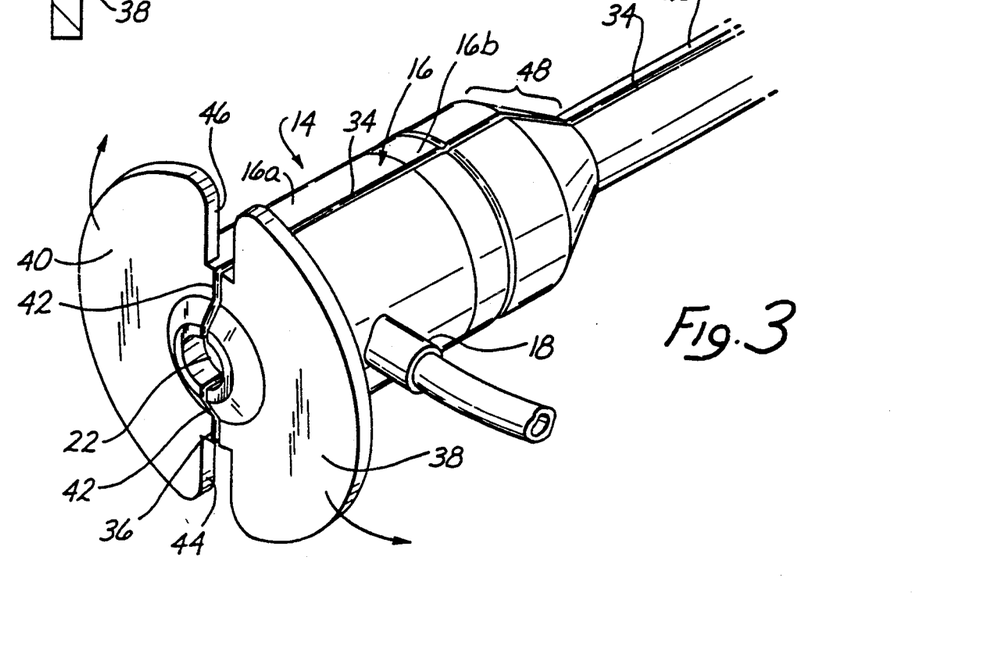
FIG. 3 is a rear prospective view of the valve and sheath combinations of FIGS. 1 and 2 showing an embodiment of diametric longitudinal score lines.

FIG. 3 illustrates in enlarged scale a rear perspective view of introducer sheath assembly 10. According to the invention, both valve assembly 14 and sheath 12 are splittable or have a peel away construction. Again, the detailed nature by which such splittable structure is implemented or how peel-away feature is realized is not critical to the invention. Any method now known or later devised by which such sheaths 12 and valve assemblies 14 may be split or separated may be employed and are contemplated as being within the scope of the invention.

In the illustrated embodiment, sheath 12 and valve assembly 14 are shown as integrally fabricated and having a pair of longitudinal score lines 34 and 36 defined along their axial length. Score lines 34 and 36 are shown as being diametrically opposed from each other across the cross section of introducer sheath 10. Intravenous sidearm 18 is depicted in FIG. 3 as being disposed between score lines 34 and 36 interlying surface between them. Score lines 34 and 36 are shown as having a V-shaped cross section but have such a shape and depth as to permit the entire length of introducer sheath 10 to be manually separated. It is contemplated that at the end of the operation the physician will grasp opposing flange portions 38 and 40 to peel them apart while pulling out the sheath and holding the lead. This will cause valve body 16 to tear along a section line depicted by dotted lines 42 through the body of valve assembly 14. Both body portions 16a and b may be scored to facilitate this tearing. In addition the bonding of the body portions 16a and 16b assists in tearing the inner body portion as the outer body portion is being torn along its corresponding tear line. The portions become through the bonding as a single body and the fracture or tear propagates from the outer body portion through the inner body portion. Membrane 22 has a weak line or score line and can easily be removed from the lead.

In the illustrated embodiment flanges 38 and 40 are formed in two halves having diametrically opposing slots 44 and 46 aligned with score lines 34 and 36 defined into valve body 16. However, it is entirely possible that score lines 34 and 36 will be continued through flanges 38 and 40 to provide deep scores instead of open slots 44 and 46.

In any case, valve body 16 is peeled apart with separation continuing through any transition portion 48 between valve body 16 and sheath 12 and on along the longitudinal length of sheath 12. Sheath 12 is then removed and peeled followed by additional removal of sheath 12 from the puncture site and peeling of the removed portions until the entire valve and introducer sheath assembly 10 of FIG. 1 has been split and removed from the lead or catheter, which is then permanently implanted into the puncture site and with which the surrounding tissue makes a blood tight seal.

Figure 4:
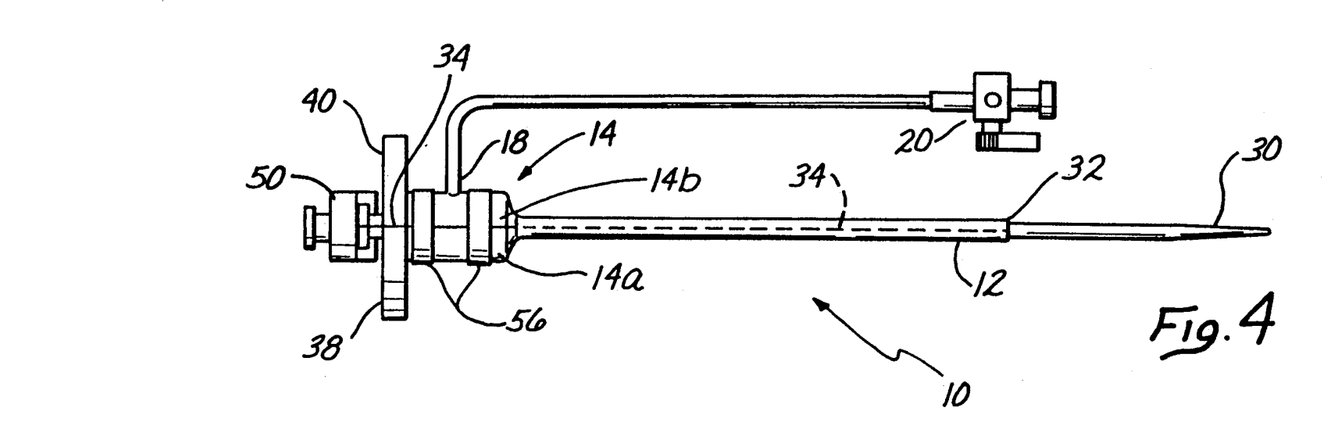
FIG. 4 is a simplified side elevational view of an additional embodiment of the invention.
Figure 5:
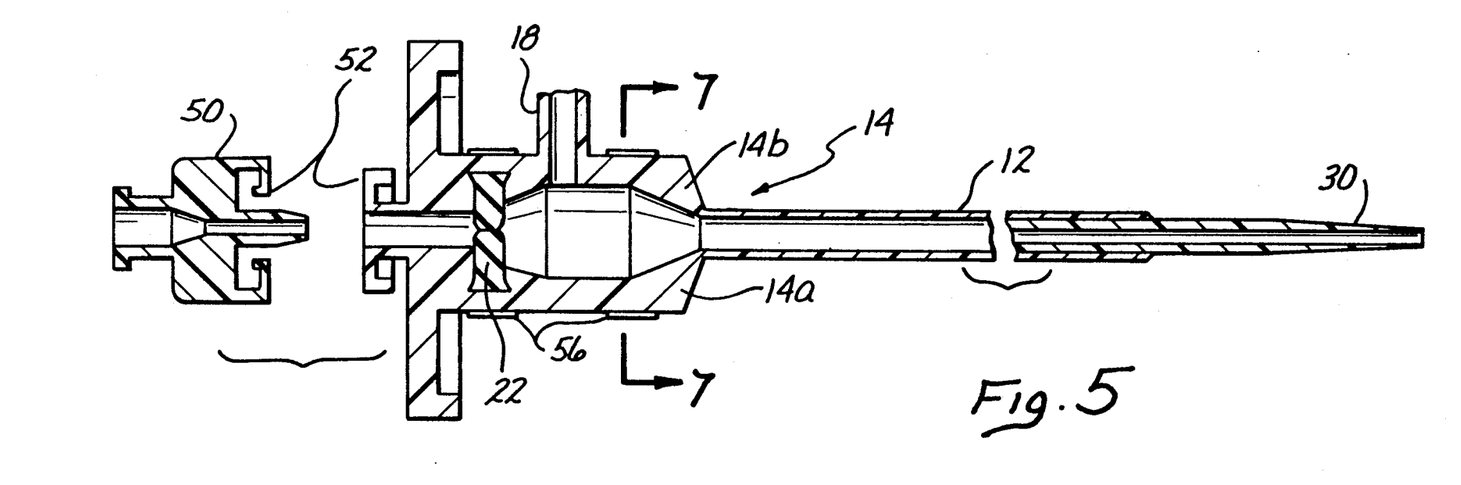
FIG. 5 is a side cross-sectional view in enlarged scale of selected cut-away portions of the hemostatic valve and sheath of FIG. 4.

The hemostatic valve and sheath 10 as seen in FIG. 1 is shown in an alternative embodiment and side elevational view in FIG. 4. In the embodiment of FIG. 4, splittable hemostatic valve assembly 14 is integrally molded or made separable from splittable sheath 12 and fitted at its proximal end with a dilator head fitting 50. Dilator head fitting 50 as shown in enlarged view in FIG. 5 is secured to valve assembly 14 by means of a conventional Luer lock 52. The score line 34 on sheath 12 continues along sheath 12 into split body portions 14a and 14b which comprise the body of valve assembly 14. Valve membrane 22, disposed within valve assembly 14, is also provided with a Y-shaped incision 54 as best depicted in the perspective view of FIG. 6 to facilitate opening and tearing of membrane 22 when valve body halves 14a and 14b are separated.

In the embodiment of FIG. 4, valve halves 14a and 14b are temporarily fixed together by means of tearable single-sided adhesive tape 56. The binding of the body portions and the hemostatic membrane need not be excessively sturdy since the device is used at low pressures, 5–10 mm Hg and its use is typically of only 10–30 minutes duration. The long leg of the Y shape incision into or through membrane 22 may or may not extend to the periphery of membrane 22 as may be needed to facilitate its tearing or cutting.

The practicing physician may then take a scalpel and easily cut tape 56 along the split line 34 and valve assembly 14 thereby separating the valve body portions 14a and 14b. As described above with the body portions 14a and 14b separated, sheath 12, which is integral, is then readily split along score line 34.

Figures 6, 7A:
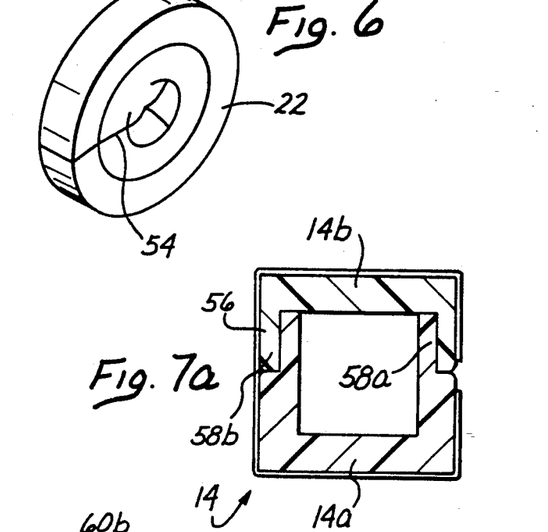
Figure 7B:
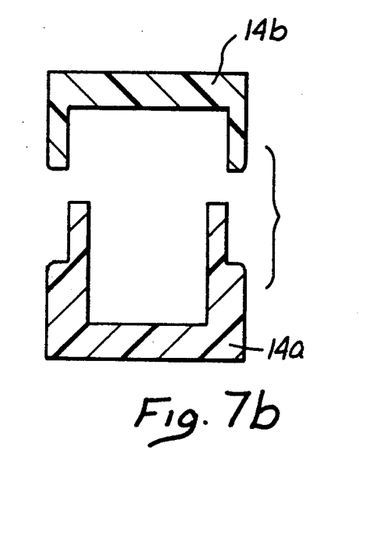

Valve body 14 may be manufactured from valve body portions 14a and 14b in a number of alternative forms. One embodiment is shown in FIG. 7a and 7b wherein valve body 14 is generally split into two halves, an upper half 14b b and a lower half 14a. Lower half 14a is provided with an interior circumferential lip 58a which slip fits into an exterior circumferential lip 58b defined in upper body half 14b. The two body halves, 14a and 14b, as shown in FIG. 7, which is a perpendicular cross-sectional view taken through section lines 7—7 of FIG. 5, are then held together using tape 56. Once the tape is cut, the two body halves may then be manually separated as depicted in FIG. 7b. While assembled, however, valve assembly 14 provides a water-tight or blood-tight valve assembly.

Figure 8:
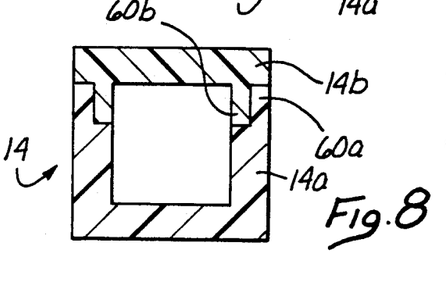
FIG. 8 shows another embodiment of the valve body in perpendicular cross-sectional view as would be seen through section line 7—7 of FIG. 5.

Another embodiment of the body of valve assembly 14 is depicted in the perpendicular cross-sectional view of FIG. 8 as would also be seen through section line 7—7. of FIG. 5. In the embodiment of FIG. 8, lower body portion 14a comprises a rectangular box, while upper body portion 14b is formed like a lid covering and seals the box-shape of body portion 14a. In the embodiment of FIG. 8, the outer circumferential seal 60a is provided on the lower body portion 14a while the inner circumferential seal 60b is defined on the upper lid body portion 14b, which is the conceptional reverse of the embodiment of FIG. 7.

Figure 9A:
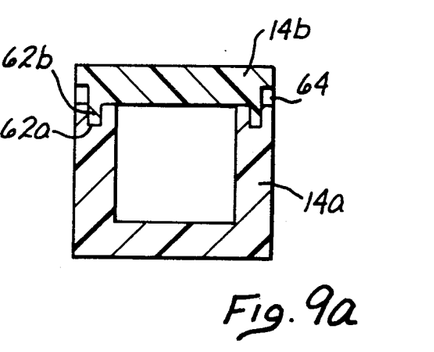
FIG. 9a is another embodiment of the valve body wherein a tongue and groove connection and pop-out indentation is provided.
Figure 9B:
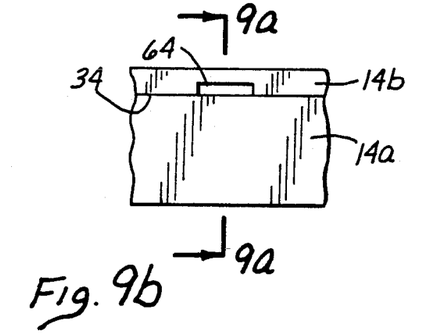
FIG. 9b is the side elevational of the valve body, the perpendicular cross-sectional of which is shown in FIG. 9a as seen through section lines 9a-9a of FIG. 9b.

FIGS. 9a and 9b illustrate yet another embodiment in which lower body portion 14a again defines a box-like shape and is coupled to upper body portion 14b acting as a lid, the two portions comprising an interior tongue and groove snap-fit. seal. In the embodiment of FIG. 9a, a, which is a perpendicular cross-sectional view as would be seen through section lines 7—7 of FIG. 5, a groove 62a is defined in lower body portion 14a while a mating tongue 62b is provided in upper lip portion 14b. Along the side of valve assembly 14 is a cut-out recess 64 in a least one position along line 34 wherein the surgeon can insert a scalpel or tool to pry body portions 14a and 14b apart. Thus, it is contemplated that at least in the embodiment of FIGS. 9a and 9b, if not other ones of the embodiment shown, that the need for tape 56 may be unnecessary in that the body portions will fit tightly together by virtue of their snap fit. The disengagement will then be affected by prying them apart, with the assistance, if necessary, of a recess 64 as depicted in FIGS. 9a and 9b.

Figure 10:
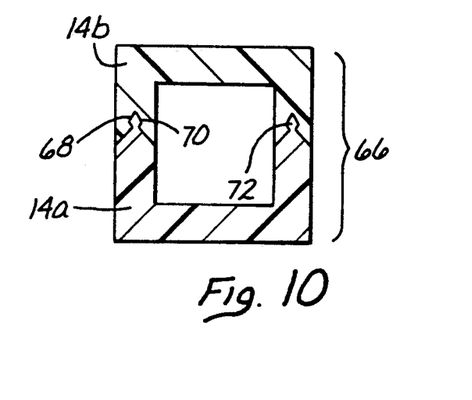
FIG. 10 is another embodiment of the valve body as seen in the perpendicular cross-sectional view as would be seen through section line 7—7 of FIG. 5.

Yet another embodiment of valve body 14 is depicted in perpendicular cross-sectional view of FIG. 10, again as would be seen through section line 7—7 of FIG. 5. In the embodiment of FIG. 10, separation between body portions 14a and 14b occurs generally along the mid-portion of lateral sides 66 of valve body 14 and are defined by providing a knife edge seal 68 in the one body portion, such as lower body portion 14a, and a conforming groove 70 in the opposing body portion, such upper portion 14b. Again, portions 14a and 14b may be held together by an 15 exterior tape 56 or may have a snap-fit facilitated by an expanded head 72 below knife edge 68 which is accommodated by a snap-fit conforming interior shape of groove 70.

It must be understood that many other embodiments may be devised by which the body portion of valve assembly 14 may be manufactured as separate halves and then be temporarily joined together with or without the aid of an exterior fastening means such as tape, friable spots of adhesive disposed in the joints between body portions 14a and 14b, or various compression fitting seals, some of which have been depicted by way of illustration in FIGS. 7-10.

Many alterations and modifications may be made by those having ordinary skill in the art without departing from the spirit and scope of the invention. Therefore, it must be expressly understood that the illustrated embodiment has been shown only for the purposes of example and should not be taken as limiting the invention which is defined by the following claims. The following claims are thus to be read as not only literally including what is set forth by the claims but also to include all equivalent elements for performing substantially the same function in substantially the same way to obtain substantially the same result even though not identical in other respects to what is shown and described in the above illustration.

I claim:

1. A sheath assembly for use with a lead or catheter comprising:
   an introducer sheath;
   a hemostatic valve coupled to said introducer sheath, said hemostatic valve and introducer sheath being arranged and configured to permit introduction of at least one lead or catheter therethrough;
   means for permitting removal of said hemostatic valve and introducer sheath from said lead or catheter disposed therethrough without requiring said introducer sheath and hemostatic valve to be removed from an end of said lead or catheter,
   wherein said means for permitting removal of said hemostatic valve comprises a two-part body, said two-part body being made in two separate body portions, said body portions defining means for sealing said body portions together when said two body parts are joined with each other to form said hemostatic valve,
   whereby said assembly may remain in a vein throughout an operation with the advantage of free lead exchange and easier lead manipulation without substantial bleeding, risk of air embolism, clotting or repeated sheath insertion causing related trauma from lead exchange, 2. The sheath assembly of claim 1 wherein said hemostatic valve comprises a resealable membrane and wherein said means for permitting the removal of said hemostatic valve comprises a cut in said resealable membrane to facilitate parting of said membrane wherein said body portions are pulled apart.

3. The sheath assembly of claim 2 wherein said cut is a Y-shaped cut extending at least partially through said membrane, the intersection of said Y-shaped cut being positioned approximately near the center of the said membrane with one leg of said Y extending toward the periphery of said membrane in a direction along which said membrane will be separated when said portions are pulled apart.

4. The sheath assembly of claim 1 wherein said means for sealing said body portions together comprise a circumferential sealing lip on each of said body portions said sealing lip on one body conforming with said sealing lip on said other body portion to make said hemostatic valve fluid-tight wherein said body portions are temporarily joined together.

5. The sheath assembly of claim 4 wherein said sealing lip on one body portion is an inner circumferential sealing lip and said sealing lip on said other body portion is an outer circumferential sealing lip, said inner and outer circumferential sealing lips conforming with each other to seal the said hemostatic valve.

6. The sheath assembly of claim 5 wherein said body portions further comprise at least one band of circumferential tape wound around said two; body portions to temporarily maintain said body portions together and to maintain: said inner and outer circumferential sealing lips in a sealed configuration.

7. The sheath assembly of claim 5 wherein said inner and outer sealing lips tightly slip-fit together to maintain said two body portions temporarily joined to comprise said hemostatic valve until pried apart.

8. The sheath assembly of claim 5 wherein said body portion having one of said circumferential sealing lips forms a lid and said body portion having said other one of said circumferential sealing lips forms an enclosure having one open side, said body portion forming said lid joining said body portion forming said enclosure to provide a temporarily fluid-tight hemostatic valve body.

9. The sheath assembly of claim 5 wherein said inner circumferential sealing lip forms a tongue and wherein said outer sealing lip forms a groove, said tongue being tightly slip-fit into said groove to form a sealed relationship between two said body portions.

10. The sheath assembly of claim 9 further comprising a recess defined in one of said body portions adapted to allow insertion of a flat blade therein to pry apart said two body portions.

11. The sheath assembly of claim 5 wherein said inner and outer circumferential sealing lips lock together by engagement with each other to seal said hemostatic valve.

12. The sheath assembly of claim 11 wheein said inner circumferential sealing lip has a knife edge and said outer circumferential sealing lip has a cavity defined therein conforming to said knife edge of said other sealing lip, said knife edge and cavity mating to form said seal of said hemostatic valve.

13. The sheath assembly of claim 12 wherein said knife edge has an enlarged head, said enlarged head being snap-fit into a conforming enlargement defined in said cavity to lock said knife edge in said cavity.

14. A method of percutaneous catherterization comprising the steps of:
   disposing an introducer sheath and hemostatic valve coupled to said introducer sheath into a body lumen;
   disposing at least one lead or catheter through said valve and introducer sheath into said body lumen;
   sealing said lead or catheter within said hemostatic valve to prevent bleeding and introduction of air into said body lumen with disposition of said lead or catheter therein; and
   later removing said hemostatic valve and introducer sheath while leaving said lead or catheter in place within said body lumen without sliding either said introducer sheath or hemostatic valve over an end of said lead or catheter,
   where in said step of removing said hemostatic valve, said hemostatic valve is comprised of two body portions, said body portions being separately provided to form said hemostatic valve and being temporarily joined together to form a complete body of said hemostatic valve, wherein said body portions are pulled apart to split said hemostatic valve;
   whereby implanted leads or catheters may be disposed into said body lumen without bleeding, risk of air embolism, clotting or repeated sheath insertion related to trauma for lead exchange or requiring said into said lead or catheter to a have structure to permit removal of said sheath and valve thereover.

15. The method of claim 14 where said step of removing said sheath and lead or catheter comprises the of splitting said sheath and valve along a longitudinal length of said sheath and valve and disposing said lead or catheter radially through said longitudinal split.

16. The method of claim 15 where said step of splitting said sheath and valve comprises a step of splitting said sheath and valve along a score line by manually tearing said sheath and prying said valve apart along said score line.

17. The method of claim 17 where said step of tearing said sheath and prying valve along a score line further comprises tearing said sheath and prying valve along a pair of longitudinally defined score lines in said sheath and valve.

18. The method of claim 17 wherein said step of prying said valve apart and tearing said sheath along a pair of score lines comprises the step of prying said valve and tearing sheath along diametrically opposing longitudinally defined score lines in said valve and sheath respectively.

19. A sheath assembly for use with a lead or catheter, comprising:
   an introducer sheath;
   a hemostatic valve coupled to said introducer sheath, said heomstatic valve and introducer sheath being arranged and configured to permit introduction of at least one lead or catheter therethrough;
   means for permitting removal of said hemostatic valve and introducer sheath from said lead or catheter disposed therethrough without requiring said introducer sheath and hemostatic valve to be removed from an end of said lead or catheter;
   wherein said means for permitting removal of said heomstatic valve comprises a multiple-part body, said body being made in at least two separate body portions, said body portions defining means for sealing said body portions together when said body parts are joined with each other to form said heomstatic valve;
   whereby said assembly may remain a vein throughout an operation with the advantage of free lead exchange and easier lead manipulation without substantial bleeding, risk of air embolism, clotting or repeated sheath insertion causing related trauma from lead exhange.

20. The sheath assembly of claim 19 wherein said multiple-part body is a two-part body.

21. The sheath assembly of claim 19 wherein said hemostatic valve comprises a releasable membrane and wherein said means for permitting the removal of said hemostatic valve comprise a cut in releasable membrane to facilitate parting of said membrane wherein said body portions are pulled apart.

22. The sheath assembly of claim 21 wherein said cut is a Y-shaped cut extending at least partially through said membrane, the insertion of said Y-shaped cut being positioned approximately near the center of the said membrane with one leg of said Y extending toward the periphery of said membrane in a direction along which is membrane will be separated when said portions are pulled apart.

23. The sheath assembly of claim 19 wherein said means for sealing said body portions together comprise a circumferential sealing lip one each of said body portions, said sealing lip on one body conforming wit a sealing lip on another of said body portions to make said heomstatic valve fluid-tight wherein said body portions are temporarily joined together.

24. The sheath assembly of clam 23 wherein said sealing lip on one body portion is an inner circumferential sealing lip and said sealing lip on said another body portion is an outer circumferential sealing lip, said inner and outer circumferential sealing lips conforming with each other to seal said hemostatic valve.

25. The sheath assembly of claim 24 wherein said inner and outer sealing lips tightly slip-fit together to maintain said two body portions temporarily joined to comprise said hemostatic valve until pried apart.

26. The sheath assembly of claim 24 wherein said body portion having one of said circumferential sealing lips forms a lid and said body portion having another of said circumferential sealing lips forms an enclosure having one open side, said body portion forming said lid joining said body portion forming said enclosure to provide a temporarily fluid tight hemostatic valve body.

27. The sheath assembly of claim 24 wherein said inner circumferential sealing lip forms a tongue and wherein said outer circumferential sealing lip forms a groove, said tongue being tightly slip-fit into said groove to form a sealed relationship between two said body portions.

28. The sheath assembly of claim 27 further comprising a recess defined on one of said body portions adapted to allow insertion of a flat blade therein to pry apart two said body portions.

29. The sheath assembly of claim 24 wherein said inner and outer circumferential sealing lips lock together by engagement with each other to seal said hemostatic valve.

30. The sheath assembly of claim 29 wherein said inner circumferential sealing lip has a knife edge and said outer circumferential sealing lip has a cavity defined therein conforming to said knife edge of said outer sealing lip, said knife edge and cavity mating to form said seal of said hemostatic valve.

31. The sheath assembly of claim 30 wherein said knife edge has an enlarged head, said enlarged head being snap-fit into a conforming enlargement defined in said cavity to lock said knife edge in said cavity.

32. The sheath assembly of claim 19 further comprising an exterior fastening means to temporarily maintain said body portions together.

33. The sheath assembly of claim 32 wherein said exterior fastening means comprises at least one band of circumferential tape wound around said body portions.

* * * * *

UNITED STATES PATENT AND TRADEMARK OFFICE
CERTIFICATE OF CORRECTION

| | |
|---|---|
| PATENT NO. | : 5,312,355 |
| APPLICATION NO. | : 07/905045 |
| DATED | : May 17, 1994 |
| INVENTOR(S) | : Hongpyo Lee |

Page 1 of 1

It is certified that error appears in the above-identified patent and that said Letters Patent is hereby corrected as shown below:

On Title Page item 45 and item [*] Notice, delete "June.30, 2009" and insert
-- July 9, 2011 --.

Signed and Sealed this

Twentieth Day of May, 2008

JON W. DUDAS
*Director of the United States Patent and Trademark Office*